United States Patent [19]

Sundman et al.

[11] 4,380,561
[45] Apr. 19, 1983

[54] TREATMENT OF WOOD USING BRANCHED-CHAIN ALIPHATIC CARBOXYLIC ACIDS

[75] Inventors: Carl-Erik Sundman, Nacka; Bengt G. Hägglund, Södertälje, both of Sweden

[73] Assignee: KenoGard A.B., Stockholm, Sweden

[21] Appl. No.: 249,658

[22] Filed: Mar. 31, 1981

[30] Foreign Application Priority Data

Apr. 28, 1980 [SE] Sweden .................................. 8003219

[51] Int. Cl.³ .................................................. C09D 5/14
[52] U.S. Cl. .................................. 427/421; 106/15.05; 106/18; 424/318; 427/429; 427/440
[58] Field of Search .................. 106/15.05, 18.32, 18; 427/440, 421, 429; 424/318

[56] References Cited

U.S. PATENT DOCUMENTS

| | | | |
|---|---|---|---|
| 2,951,789 | 9/1960 | McCants | 167/38.5 |
| 3,558,782 | 1/1971 | Rutkowski | 424/291 |
| 4,061,500 | 12/1977 | Hager | 106/18 |
| 4,193,993 | 3/1980 | Hilditch | 424/141 |

FOREIGN PATENT DOCUMENTS

| | | |
|---|---|---|
| 5361 | 11/1979 | European Pat. Off. |
| 929090 | 7/1949 | Fed. Rep. of Germany. |
| 932453 | 9/1955 | Fed. Rep. of Germany. |
| 1037761 | 8/1966 | United Kingdom. |

*Primary Examiner*—Lorenzo B. Hayes
*Attorney, Agent, or Firm*—Fred Philpitt

[57] ABSTRACT

Branched-chain aliphatic carboxylic acids, or their alkali- or ammonium salts, are used for the protection of wood and other cellulose-based materials against attacks of sapstain and mould fungi. The acids contain 6 to 20 carbon atoms and are iso-acids or acids which are mono-branched in 2-position. 2-ethyl hexanoic acid, or its salts, is particularly preferred. The acids are particularly suitable for short-term protection treatment of wood. The acids can be applied in the form of water solutions or dispersions by means of dipping, coating or brushing.

3 Claims, No Drawings

TREATMENT OF WOOD USING BRANCHED-CHAIN ALIPHATIC CARBOXYLIC ACIDS

The present invention relates to the use of certain branched-chain aliphatic carboxylic acids, such as 2-ethyl hexanoic acid, or alkali- or ammonium salts of these acids, for the treatment of wood and other wood-based materials for protection against attack from sapstain and mould fungi.

The main groups of wood destroying fungi are the sapstain and mould-fungi and the rot fungi. In order to confer to wood and other materials a good and lasting protection against attack orf rot fungi it is, in most cases, necessary to use complicated methods such as impregnation under pressure to obtain a sufficient penetration, retention and fixation of the active agents. Protection against mould and sapstain fungi can generally be obtained by simpler methods such as dipping, spraying and brushing. Materials which will be in a lasting contact with soil and water are protected against rot. When materials are treated for protection against sapstain and mould fungi the intention is often to obtain a protection only for a shorter period of time, e.g. during the time for air-drying timber in timber yards before it is further treated. Even if it is not necessary to get a lasting protection at the treatment against sapstain it is essential that the treatment gives a good protection, not only in order to avoid the miscoloration resulting from attack of sapstain fungi but also as such attacks make the materials more susceptible to attack of rot.

The most commonly used preservatives against sapstain and mould fungi are based on pentachlorophenols. Use of normal, i.e. straight-chained, fatty acids has also been suggested for this purpose, U.S. Pat. No. 4,061,500. Most compositions for rot-protection are based on so-called preservative metals, e.g. copper, chromium and arsenic. When the aim of the wood protecting treatment is mainly directed to avoidance of attack from sapstain fungi it is of course desirable not to use agents which in themselves give rise to miscoloration of the surfaces of the treated material and copper-based agents are thus unsuitable for this purpose. It is of course also desirable to avoid preservative metals with respect to their negative effects on the environment. As has been mentioned above, it is in most cases necessary to use metal-based agents for rot-protection, as a long-lasting protection is desired by this treatment. It is also known to use e.g. copper salts of fatty acids for rot-protection and a development of these agents are the compositions described in the U.S. patent specification No. 4,193,993. The compositions according to that patent contain combinations of preservative metals and branched-chain carboxylic acids. The compositions have several fungicidal uses and are used both as wood preservatives and agricultural fungicides. As wood preservatives the compositions have been used for pressure impregnation against rot.

It has now been found that a very satisfactory protection of wood and other fibre materials against sapstain and mould fungi can be obtained by using certain branched-chain aliphatic carboxylic acids. The obtained effect is substantially better than the effect obtained using the corresponding normal fatty acids and use of the branched-chain acids also have other advantages.

The present invention thus relates to the treatment of wood and wood-based products, such as particle board and board, for protection against sapstain- and mould fungi using branched-chain aliphatic carboxylic acids containing 6 to 20 carbon atoms, or their alkali- or ammonium salts, which acids are mono-branched in 2-position or are iso-acids. The treatment is carried out by dipping, spraying or coating.

The branched aliphatic carboxylic acids which in free form, or in the form of salts as above, can be used for the treatment according to the invention contain totally 6 to 20 carbon atoms, suitably 7 to 13 carbon atoms and preferably 8 to 12. The acids are iso-acids or contain one branch in 2- position (alpha-position). The length of the branches can vary as long as the total number of carbon atoms is within the stated range. The branches should, however, preferably be short relative to the chain and are suitably methyl- or ethyl groups. As examples of suitable acids can be mentioned 2-ethyl butanoic acid, iso-octanoic acid, 2- ethyl hexanoic acid, iso-nonanoic acid, iso-tridecanoic acid and iso-octadecanoic acid. Combination of two or more branched-chain acids can of course also be used. The most preferred acid is 2-ethyl hexanoic acid.

The acids can be used in free form or in the form of their alkali salts, i.e. sodium- or potassium salt, or as ammonium salt. The salt-form is preferred since the acid in this form is very easily soluble in water. There are no problems encountered in the preparation of the salts and satisfactory water solutions of the salts are obtained whether there is an excess of alkali or ammonium with respect to the acid or not. The solutions have a very good stability and additional additives to prolong the handleability before use are generally not required. It is particularly preferable to use ammonium salts for the material to be protected, as the ammonium ion in these salts is evaporated after application and hereby the acid is better fixed to the fibre materials.

The branched-chain acids are used for protective treatment of wood and other cellulose-fibre based materials, such as particle board and board, against attack of sapstain and mould fungi and conventional methods for this treatment can be used. The active agents are suitably applied by means of dipping, spraying or brushing. From a practical point of view and with respect to environment it is preferred that the acid, or its alkali or ammonium salt, is used in the form of water dispersions or water solutions. Solvents, such as e.g. white spirit, can of course be used if desired. The amount of active fungicide, according to the invention in the treatment solutions should be at least 0.1 percent to give an effective amount of retained active substance in the treated materials. The upper limit is not critical but is mainly decided with respect to economy and, as for the lower limit, with respect to the material to be treated and the desired effect. The upper limit is generally not about 10 percent by weight, and the amount of active substance in the treatment solutions is suitably within the range of 1 to 10 percent by weight.

The branched-chain aliphatic acids and their salts do not give rise to miscoloration of the treated materials, nor do they give rise to negative effects on the environment. The substances can be used in solutions having pH-values within a fairly broad range. The treatment solutions can also contain additives such as antifoaming agents and buffer substances. As examples of the latter kind of additives can be mentioned carbonates, phosphates and borates.

Although the branched-chain acids and their salts can be used for protection of other materials than wood against sapstain and mould fungi, the protection of wood is particularly preferred and then for so-called short-term protection, i.e. treatment of wood for protection during a limited period of time before the wood is further treated. In contrast to treatment for rot-protection which generally is carried out in order to obtain protection during a very large number of years, short-term protection is carried out to give protection for a period of time generally within the range of from three months to one year or a couple of years. The use of the acids, or their salts, does not give rise to any substantial negative effects with respect to subsequent treatment of the wood such as glueing and painting.

The invention is further illustrated in the following examples, which however are not intended to limit the same.

EXAMPLE 1

The fungicidal effect of heptanoic acid, pelargonic acid and 2-ethyl hexanoic acid was investigated. Four different sapstain fungi (*Pullularia pullulans, Cladosporium herbarum, Scopularia phycomyces* and *Ceratocystis coeruleum*)and three different mould fungi (*Penicillium sp., Alternaria sp.* and *Trichoderma sp.*) were used as test organisms.

Fresh cut discs of pine having a thickness of 8 mm and a diameter of 4–7 cm were dipped into a spore solution of the above mentioned fungi. The discs were then dipped into treatment baths containing water dispersions of the mentioned acids in varying concentrations. The discs were dipped into the treatment baths for 15 seconds and were then placed in closed plastic containers containing water. The discs were placed above the water surface and the containers were kept at a temperature of 20° C.

Between each series of discs treated with the same product a reference disc was placed and this disc had only been dipped into the spore solution. The attack was inspected after 14, 21, 31 and 53 days and evaluated visually according to the following scale: 0=no attack, 1=tendency to attack, 2=attack, 3=severe attack, 4=very severe attack. These values correspond roughly to the following percentage of attacked surface: 0=0%, 1=0–2%, 2=5–20%, 3=25–50% and 4=more than 50%.

The results are shown in the table below.

| Fungicidal substance | Concentration percent by weight in treatment bath | Test results (after stated number of days) | | | |
| --- | --- | --- | --- | --- | --- |
| | | 14 | 21 | 31 | 53 |
| Heptanoic acid | 1.1 | 0 | 0 | 4 | 4 |
| | 1.8 | 0 | 1 | 3 | 4 |
| | 2.6 | 0 | 3.5 | 4 | 4 |
| | 3.9 | 1 | 3 | 4 | 4 |
| Reference | — | 2.5 | 3 | 4 | 4 |
| Pelargonic acid | 1.1 | 3 | 3.5 | 4 | 4 |
| | 1.8 | 1.5 | 3 | 4 | 4 |
| | 2.6 | 1 | 2.5 | 4 | 4 |
| | 3.9 | 1.5 | 1.5 | 3 | 3.5 |
| Reference | — | 3 | 4 | 4 | 4 |
| 2-ethylhexanoic acid | 1.1 | 0.5 | 0 | 0 | 0 |
| | 1.8 | 0 | 0 | 0 | 0 |
| | 2.6 | 0 | 0 | 0 | 0 |
| | 3.9 | 0 | 0 | 0 | 0 |
| Reference | — | 1 | 3 | 3 | 4 |

EXAMPLE 2

The effect of sodium-2-ethyl hexanoate and ammonium-2-ethyl hexanoate against blue and mould fungi was investigated according to the following.

Fresh cut discs of pine were dipped into a spore solution of the same kind as the one used in Example 1. A reference disc was picked-out for each test and for each test two discs were picked-out for 15 seconds dipped into water solutions having different concentrations of the mentioned salts. The three discs for each test were then placed in plastic bags which were closed. The attack of fungi was evaluated visually after 7, 14 and 21 days respectively, according to the same scale as in Example 1. The results are shown in the table below.

| Fungicidal substance | Concentration percent by weight in treatment bath | Test results (after mentioned number of days) | | | | | |
| --- | --- | --- | --- | --- | --- | --- | --- |
| | | 7 | | 14 | | 21 | |
| | | Treated | Reference | Treated | Reference | Treated | Reference |
| Sodium-2-ethyl hexanoate | 1 | 0 | 4 | 2.5 | 4 | 2 | 4 |
| | 2 | 0 | 3 | 1 | 4 | 1 | 4 |
| | 4 | 0 | 3 | 0 | 4 | 0 | 4 |
| | 6 | 0 | 4 | 0 | 4 | 0 | 4 |
| | 8 | 0 | 2 | 0 | 4 | 0 | 4 |
| Ammonium-2-ethyl hexanoate | 1 | 2 | 3 | 2.5 | 4 | 3 | 4 |
| | 2 | 0 | 4 | 0 | 4 | 1 | 4 |
| | 4 | 0 | 4 | 0 | 4 | 0 | 4 |
| | 6 | 0 | 3 | 0 | 4 | 0 | 4 |
| | 8 | 0 | 3 | 0 | 4 | 0 | 4 |

EXAMPLE 3

50×100 mm lumber having a length of 3 to 5 meters were dipped manually into different water-based treatment solutions and the lumber was thereafter stored stock-piled outdoors in a timber yard. Each layer contained 10 boards. A total number of 30 boards were dipped into each treatment solution. Attack of mould and sapstain fungi and rot was inspected after 7 and 10 months storage respectively. The evaluation was carried out according to the same scale as in Example 1 and the results are shown in the table below.

| Fungicidal substance | Concentration percent by weight in the treatment solution | Test results (after mentioned number of months) | |
|---|---|---|---|
| | | 7 months | 10 months |
| Reference untreated | — | 3.5–4 | 4 |
| Ammonium-2-ethyl-hexanoate | 2 | 0 | 0–4 |
| | 5 | 0 | 1–2.5 |
| Ammoniumcaprylate | 2 | 1–2.5 | 4 |
| | 5 | 0.5 | 4 |

We claim:

1. A method for treating wood and woodbased materials such as particle board and board, for protection against attack of sapstain and mould fungi by means of dipping, spraying or brushing wherein said materials are treated with a composition which consists of water and, as its active ingredient, a branched-chain aliphatic carboxylic acid, or its alkali- or ammonium salt, which acid contains totally 6 to 20 carbon atoms, wherein the acid is an isoacid or a 2- position mono-branched acid.

2. A method according to claim 1, characterized in that the branched aliphatic carboxylic acid contains 8 to 12 carbon atoms.

3. A method according to claim 1, characterized in that the branched aliphatic carboxylic acid is 2-ethyl-hexanoic acid.

* * * * *